United States Patent
Kunkel

(10) Patent No.: US 6,491,696 B1
(45) Date of Patent: Dec. 10, 2002

(54) DEVICE FOR DISTRACTING BONE SEGMENTS, ESPECIALLY IN THE AREA OF A JAW

(75) Inventor: Martin Kunkel, Mainz (DE)

(73) Assignee: Medicon Chirurgiemechaniker-Genossenschaft (DE)

( * ) Notice: Subject to any disclaimer, the term of this patent is extended or adjusted under 35 U.S.C. 154(b) by 0 days.

(21) Appl. No.: 09/700,885

(22) PCT Filed: May 20, 1999

(86) PCT No.: PCT/EP99/03471

§ 371 (c)(1),
(2), (4) Date: Mar. 6, 2001

(87) PCT Pub. No.: WO99/59491

PCT Pub. Date: Nov. 25, 1999

(30) Foreign Application Priority Data

May 20, 1998 (DE) .......................... 198 22 802

(51) Int. Cl.⁷ ................................. A61F 2/38
(52) U.S. Cl. ................. 606/105; 606/62; 606/63
(58) Field of Search ................. 606/62, 65, 63, 606/57, 58, 72, 105; 433/172, 173, 174, 176

(56) References Cited

U.S. PATENT DOCUMENTS 5,704,938 A * 1/1998 Staehlin et al.
6,126,662 A * 10/2000 Carmichael et al.
6,306,143 B1 * 10/2001 Kvarnstrom et al.

* cited by examiner

*Primary Examiner*—Pedro Philogene

(57) ABSTRACT

The invention relates to a device for distracting bone segments, comprising at least two components (12, 13) which can be displaced in relation to each other by means of an adjustment device (14) such that a distance between them is increased. According to the invention the first component (12) is configured as an outer sleeve, a second component (13) is configured as an at least partly inner sleeve which is at least partly positioned within the outer sleeve (12), the outer and inner sleeves (12, 13) can be at least partly inserted into a hole in the bone segments (19, 21) and the inner sleeve (13) engages one bone segment (19) and the outer sleeve (12) another bone segment (21).

29 Claims, 2 Drawing Sheets

DEVICE FOR DISTRACTING BONE SEGMENTS, ESPECIALLY IN THE AREA OF A JAW

Figure 1:
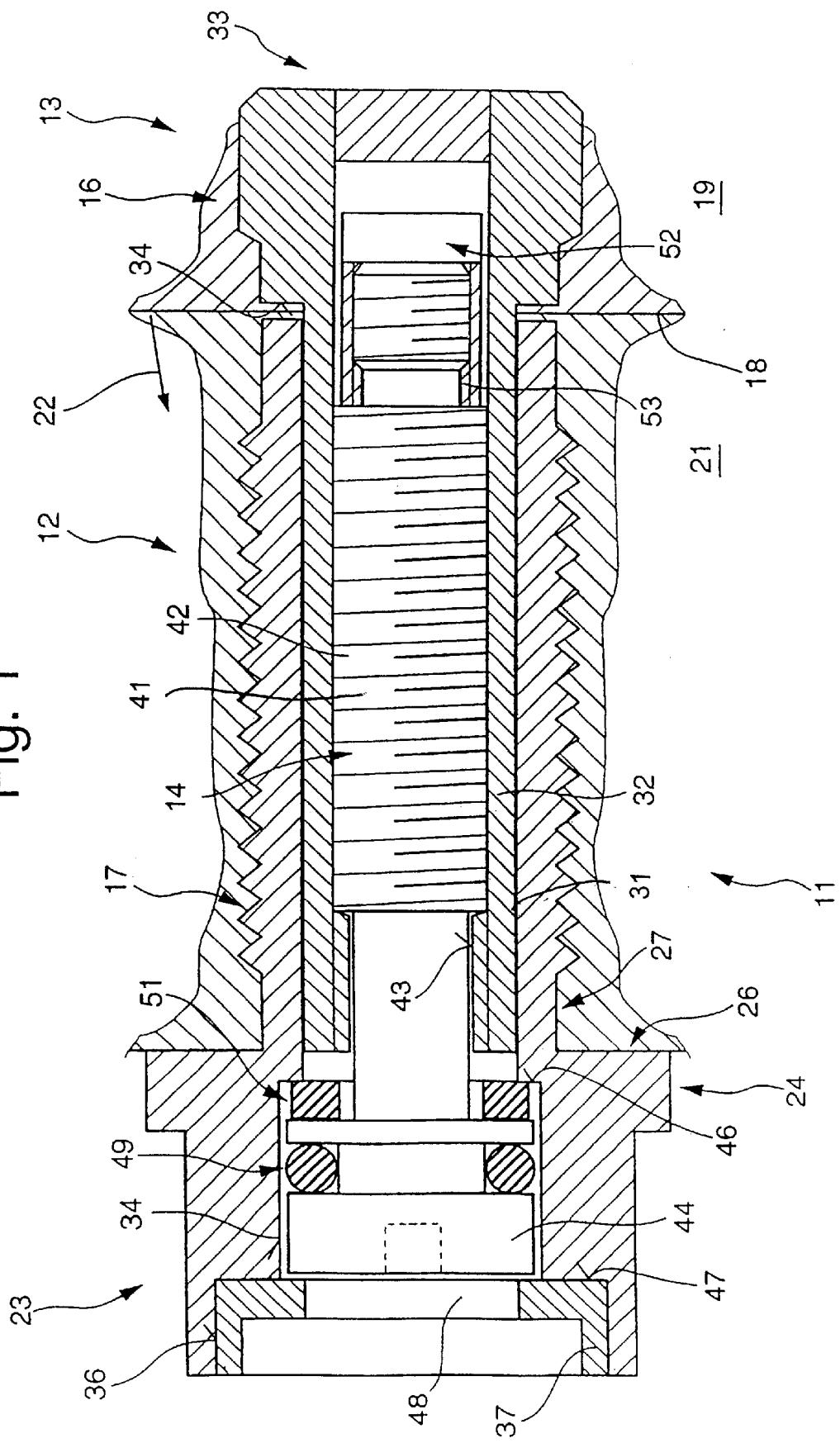

The invention relates to a device for the distraction of bone segments, particularly in the jaw region, according to the preamble of claim 1.

Such a device is known, for example, from the International Patent WO 94/22400. This device has two components whose mutual spacing is variable and which are positioned relative to one another by means of guide rods. A threaded spindle, arranged between the guide rods, is provided for varying the spacing. At right angles to the threaded spindle, a drive shaft is connected via a bevel gear to a threaded spindle in order to variably set the distance of the two components relative to each other. In order to fasten the two components to the bone segments, they respectively have several perforated plates arranged in a plane, in order to fasten the components to the bone segments by means of fixing pins or screws.

Such devices have a considerable structural size. In addition, such devices are principally suitable for use in the skull or face region. A use in the jaw region can admittedly be provided in the lateral lower jaw, but fitting is problematic because of the structural size, and accessibility is greatly impeded. For example, a nerve whose position is difficult to identify runs in the lateral region of the jaw, so that there is a very great danger of damage, particularly with such devices. In the lower jaw, this can lead to a numb lower lip. In the anterior jaw, accessibility to external devices is limited by important muscle structures.

For the reconstruction of, for example, vertical bone deficits, the use of such devices, or of devices used with such a device, is only possible with considerable tissue traumatization. Such reconstructions are required because the lack of functional loading of force application leads to atrophy of the alveolar process in the upper and lower jaw due to inactivity, and this therefore recedes.

For the reconstruction of larger vertical bone deficits, for example, of the alveolar process in the upper and lower jaw, the augmentation takes place at that time with a free bone transplant, which is usually removed as a pelvic chip in order to implant this into the jaw bone. The soft tissues are then mobilized, drawn over the bone transplant, and sewn. In this technique for vertical bone augmentation, a soft tissue correction usually has to be undertaken for the restoration of the buccal cavity. This procedure has the disadvantage that several operations are necessary; the patient has on the one hand to undergo a surgical operation, and moreover is burdened with a removal morbidity. Furthermore, the patient cannot regain his employed life for a longer time. Since the retrogression of the bone after tooth extraction mostly occurs in patients of advanced age, further dangers, such as for example thromboses, embolisms, hemorrhage or the like, have to be taken into account in connection with the above-described reconstruction of large bone deficits.

Reconstruction by implants is necessary for the production and maintenance of a denture foundation in order to fully restore the function of mastication.

The invention therefore has as its object to provide a device with which removal morbidity is avoided, building up of bone is attained in a shorter time, and a simple positioning of the device, and also its removal without problems after the bone deficit has been built up, are made possible. Furthermore, this device is to act mechanically as close as possible to the location of the distraction, and is to make possible, after removal, a simple introduction of the implant.

This object is attained according to the invention by the device according to claim 1.

The arrangement within the bone to be built up makes it possible for the mechanical action to take place at the exact place at which bone formation takes place by the very vigorous healing tissue, the so-called callus. In particular, in use for reconstruction of the jaw ridge in the upper and lower jaw by vertical callus distraction, a fine bone cut can be sawn in a jaw which is too flat, so that the portion previously bearing teeth can be moved a little. The device according to the invention is preferably provided at this place of the future artificial tooth root or of the implant, and the bone segment can be raised up with it in a controlled manner so that callus tissue forms and can lead to the reconstruction of the bone. Muscle forces which come into play can easily be compensated by this arrangement, since the mechanical action of the distraction device can be exerted directly at the place to be acted on.

Furthermore, this device has the advantage that a single tooth segment in the jaw region, that is, the denture foundation for a single tooth, can be rehabilitated. Moreover, a combination of several distraction devices can be provided, matched to the size or length of the bone segment to be distracted.

The device according to the invention has the further advantage that the soft tissues in the buccal vestibule and buccal cavity are not required in order to cover the bone implant from the pelvic region. The soft tissue correction usually necessary in the alternative procedures can thereby be omitted. The soft tissues can instead grow in parallel with the callus. Furthermore, removal morbidity, which can entail chronic pain in the pelvic region, hemorrhages, or the like, can be avoided.

An advantageous constitution of the invention provides that the maximum diameter of the outer and/or inner sleeve of the device according to the invention is of the same size as, or at least slightly smaller than, the diameter of the dental implant. As a result, the dental implant can be inserted after the removal of the distraction device, without further surgical operations being necessary. For example, the implant can then be immediately screwed in and fastened. The treatment times can thus be shortened. Moreover, an operation of this kind can be performed by dentists, without a stay in a clinic being necessary.

According to a further advantageous constitution of the invention, it is provided that a section with an external thread is provided at least partially on the inner and outer sleeves. It can thereby be made possible for the device to be inserted or screwed in a simple manner into a bore of the bone, without furthermore requiring for this purpose, fastening means which would be problematic to install particularly in the case of bone ridge widening.

According to a further advantageous constitution, it is provided that the external thread of the inner and outer sleeves is made of equal diameter. A bore in the bone section to be widened can then be established with a bone drill, in order to subsequently set the device internally of the bone, directly or indirectly.

It can furthermore be advantageously provided that the external threads of the inner and outer sleeves are formed as self-tapping threads. An insertion of the device into the bone section to be widened, directly after the bore is formed, can thereby be made possible.

So that a simple insertion and removal of the device can be made possible, it is advantageously provided that the inner and outer sleeves are guided, mutually secured against torsion. The device can thus be inserted and removed as a unit.

It is furthermore advantageously provided, for the simplification of handling, that the outer sleeve of the device has a mounting section constructed to receive a tool wrench. This mounting section can, for example, have a polygonal head, and can be, for example, a hexagonal nut or the like, so that the device can be positioned and also removed with a tool wrench.

According to a further advantageous constitution of the invention, it is provided that the mounting section of the outer sleeve is constructed as a receiving section for a dental implant. It can thereby be made possible that the distraction device no longer needs to be removed after a callus distraction, and can serve as the denture foundation. The medical operations for the construction of a dental implant can thereby be further reduced.

According to a further advantageous constitution of the invention, it is provided that the adjusting device is mechanically constructed and includes a threaded spindle which is arranged in a threaded section of the inner sleeve, and that a head of the threaded spindle is fastened axially to the external sleeve. The mechanical constitution of the distraction device makes possible a precise adjustment of the rate of distraction, which can be, for example, 0.25 mm to 0.5 mm per day. The rate of distraction can be precisely set by the number of turns, in dependence on the different constitution of the thread pitch. Furthermore, it can be advantageously attained by the securement against torsion that the rotational movement can be converted into an axial path movement or longitudinal movement.

A head of the threaded spindle is advantageously fastened in the outer sleeve, with the head situated near the mounting section of the distraction device. Good accessibility for the extension is thereby provided, since the mounting head protrudes through a soft tissue opening and accessibility can thus be given for the purpose of extension.

According to a further alternative embodiment of the invention, it is provided that the adjustment device is constituted as an osmotic pressure chamber with a semipermeable wall. It can thereby be made possible, by means of the concentration equalization of, for example, sodium chloride solutions, for the inner sleeve to be movable relative to the outer sleeve. The maximum displacement path can be determinable by means of the degree of the concentration difference.

A further alternative embodiment of the adjusting device is provided by a pressure spring mechanism which makes possible a continuously adjustable, or for example finely stepped, rate of distraction. The device can furthermore have an adjusting device which is actuatable by means of compressible materials, preferably with air-elastic or rubber-elastic materials.

Further advantageous embodiments of the invention are described in the further claims.

A preferred embodiment example of the invention is described in further detail hereinbelow.

Figure 2:
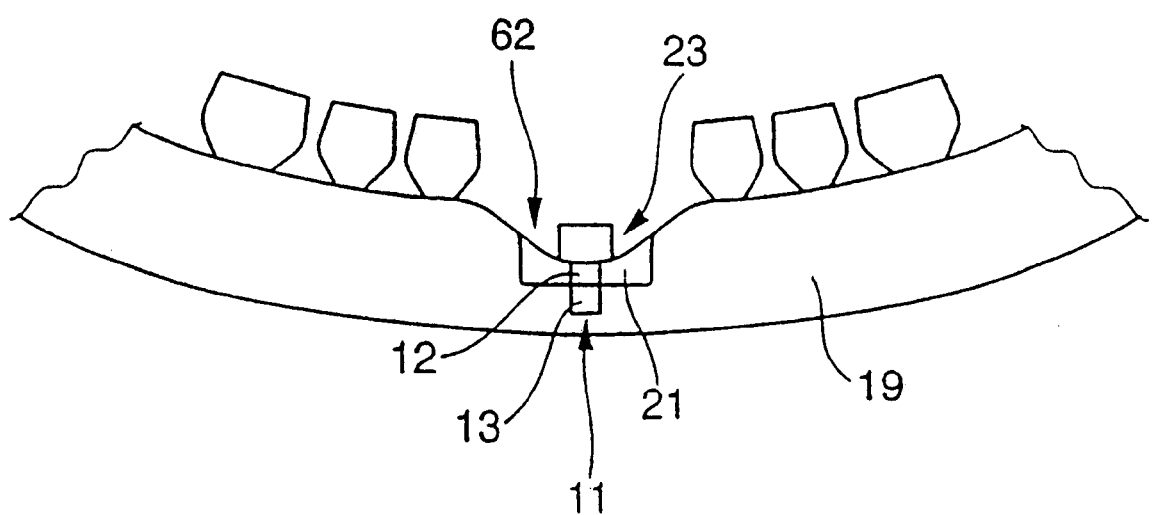

FIG. 1 shows a schematic, enlarged sectional illustration of the device according to the invention, and FIG. 2 shows a schematic illustration of a case of application of the device according to the invention.

A schematic, enlarged illustration in cross section of the distraction device 11 according to the invention is shown in FIG. 1. The distraction device 11 according to the invention is provided for a callus distraction. The distraction device 11 is preferably used for jaw ridge augmentation, or for the reconstruction of the atrophied alveolar process in the upper and lower jaw by vertical callus distraction. It is of course self-evident that the distraction device 11 according to the invention can be used, not only in the jaw region, but also in all other regions which are suitable for the device according to the invention. The device 11 according to the invention and its constitution according to the invention will be described hereinbelow in its use for jaw ridge augmentation on the lower jaw, by way of example.

The distraction device 11 has an outer sleeve 12, within which an inner sleeve 13 is at least partially guided. By means of an adjusting device 14, the outer sleeve 12 and inner sleeve 13 are adjustable in mutual distance and mutually variable in size.

The distraction device 11 is inserted into a bore of a jaw ridge 19 from which there is sawn out before or even thereafter a bone segment 21 which is variable in distance to the jaw ridge 19 for the formation of the callus.

For example, as shown in FIG. 2, the inner sleeve 13 is arranged with an outer thread 16 in the jaw ridge 19, the outer sleeve 12 being arranged with an external thread 17 in a bore section of the sawn-out bone segment 21. A line 18 in FIG. 1 represents the line of intersection between the jaw ridge 19 and the bone segment 21. The distraction device 11 executes an extension, so that the outer sleeve 12 is movable with the bone segment 21 in the direction of the arrow 22, so that the distance between the jaw ridge 19 and the bone segment 21 is variable.

The outer sleeve 12 essentially consists of four regions, with a first region being constituted as a mounting section 23, and a second region as an annular shoulder 24 with an abutment face 26, merging into a third region, a section 27 without threads. This is adjoined by a fourth region, which has an external thread 17. The mounting section 23 is constituted, for example, as a hexagonal nut, so that the distraction device can be screwed with a tool wrench into a bore. The mounting section 23 can have further alternative forms of embodiment which are suitable for receiving or application of a tool wrench, in order to position the distraction device 11 in a bore and to remove it again. Seen in the direction of the mounting section 23, the annular shoulder 24, which is formed with a greater diameter than the mounting section 23, forms a boundary of the mounting section 23, so that the tool wrench can be put on only up to a given region on the mounting section 23 and does not damage the soft tissues. By means of the abutment surface 26, the annular shoulder 24 forms a boundary for the screwing in and positioning of the distraction device 11 in the bore of the jaw ridge 19. The abutment surface 26, and also the thread-free section 27, are preferably constituted as polished surfaces. These abut against the soft tissue in the inserted state of the distraction device. In the exemplary embodiment, these surfaces abut on the gum or on the bone. Alternatively, it can also be provided that a cup-shaped transition is formed between the external thread 17 and the mounting head 23, and serves for the shaping of the future gum edge. The external thread 17 of the outer sleeve 12 engages in the sawn-out and movable bone segment 21.

The inner sleeve 13 is fixed with the external thread 16 in the jaw ridge 19, and is supported on this during the distraction. It is advantageously provided that the external thread 16 of the inner sleeve 13 and the external thread 17 of the outer sleeve 12 are constituted equal in diameter. Thereby, a bore can be set in one working step, and the distraction device 11 can then be easily fixed. Alternatively, a two-step form of the distraction device 11 can be provided, the external thread 16 of the inner sleeve 13 being smaller in diameter than the external thread 17 of the outer sleeve 12. A two-step bore is advantageously formed in the bone in this embodiment.

The external threads 16, 17 are advantageously provided as self-tapping threads, giving a simple and rapid mounting of the distraction device 11. The working step of thread cutting can then be saved.

The outer sleeve 12 has a first bore 31 in which the guide section 32 of the inner sleeve 13 is arranged. The first bore 31 and the guide section 32 can be mated together such that an arrangement is given which is secured against torsion. This can be provided, for example, by the formation of a polygonal bore 31. Alternatively, further securements against torsion can be made possible, which are fit for use because of the distraction device being bodily constituted very small in scale.

Outside the outer sleeve 12, a further tubular section adjoins the guide section 32, and has a thread section 16. This can be connected, for example integrally, to the tubular section or can be set on the tubular section as a pressed part or by other means. The tubular guide section 32, at its section situated outside the outer sleeve 12, is closed medium-tight with a closure cap 33. The closure cap 33 can be fastened in the tubular section by the usual techniques, or is advantageously fixed by laser welding. The threaded section 16 has a stop surface 34 at its end facing toward the outer sleeve 12, and the distraction device is thereby fixed with respect to its shortest structural size, provided that the stop surface 34 abuts on the corresponding surface of the outer sleeve 12.

The outer sleeve 12 has a through bore with three sections. A first section forms the first bore 31 to receive the guide section 32 of the inner sleeve 13. A second section is formed by the second bore 34, which is of greater diameter than the first bore 31 and receives important portions of the setting device 14. Therein a third bore 36 adjoins the mounting section 23 and is again constituted greater in diameter than the second bore 34, and receives a securing bushing 37.

The adjusting device 14 is provided as a mechanical adjusting device in the present preferred embodiment example, and has a threaded spindle 41 which engages with its thread 42 on an internal thread 43 of the inner sleeve 13. The internal thread 43 is arranged at an end of the inner sleeve 13 opposite the external thread 16. The threaded spindle 41 has a spindle head 44 for its actuation, having a slot to receive a screwdriver for actuating it. A cross slot, hexagonal socket, or the like can likewise be provided. The spindle head 44 is arranged near to the free end of the mounting section 23, so as to give good accessibility with a tool wrench. The spindle head 44 of the threaded spindle 41 is fixed axially of the external sleeve 12. On the one hand, the spindle head 44 is supported directly or indirectly on a shoulder 46, which is formed by the transition from the first bore 31 to the second bore 34. Furthermore, the spindle head 44 is axially fastened by the securing bushing 37 which slightly projects radially over the shoulder 47 and has an opening 48 to make accessibility to the spindle head 44 possible. The securing bushing 37 is advantageously pressed into the mounting section 23. Further suitable possibilities of fixing can likewise be given.

In the preferred embodiment example, a medium-tight constitution of the distraction device 11 is shown, which can be selectively provided. On the one hand, the closure cap 33 is provided for this purpose on the inner sleeve 13. On the other hand, a radial shaft sealing ring 49 is provided on the spindle head 44, making it possible to be able to interrupt a free passage from the exterior via the third, second and first bore 36, 34, 31 into the distraction region, or vice versa. It can furthermore be provided that instead of the radial shaft sealing ring 49, a closure stopper can be inserted on the mounting section 23 or in this. This can for example be constituted of plastic. An antibacterial ointment or a sliding sealing means can advantageously be arranged therebetween.

The threaded spindle 41 is rotatably mounted on the first shoulder 46 via a washer 51. This can minimize, for example, the frictional forces during the rotation process. Furthermore, for easy accessibility of the distraction device 11, it is provided that a slight play is provided between the guide section 32 and the first bore 31, so that a slight axial movement can be given for increasing the space between the external thread 16 of the inner sleeve 13 and the external thread 17 of the inner sleeve 12.

The maximum displacement path of the distraction device 11 is put into effect by a locking element 52. This locking element 52 is fastened to a thread stub 53 at the free end of the threaded spindle 41. The diameter of the locking element 52 is set such that this projects at least partially over the minor diameter of the thread 42, so that with a movement of the inner sleeve 13 to the right, the internal thread 43 of the guide section 32 abuts on the locking element 52.

The distraction device 11 is advantageously constituted of biocompatible material which has a minimum toughness so that the thread turns of the external threads 16, 17 do not become stripped. For example, a titanium alloy or implant steel can be provided. At least the outer portions which come into contact with the tissue must be constituted of compatible material. Thus the threaded spindle 41, for example, can be constituted from an alloy or a material different from that of the outer sleeve 12 and inner sleeve 13, and also from that of the securing bushing 37 and the closure cap 33.

The external thread diameter 16, 17 is at least the commercially available 3.5 mm through 4.2 mm. For example, a small embodiment can be between 3.7 mm and 4 mm in diameter. This measurement is suited to the implant diameter, for example for artificial tooth roots, which typically have an external diameter of 4 mm. Simple insertion of the artificial tooth root can thereby be made possible after the callus distraction and after the removal of the distraction device 11, without further surgical measures being necessary.

If the distraction device 11 is to form a portion of the dental implant, it is advantageously provided that the mounting section 23, for example, an external or internal thread, has a further suitable receiver in order to be able to fix thereon the implant, for example a crown. It can furthermore be provided that adapter members for an implant structure can be installed thereon.

The device according to the invention can also be used, for example, in a manner such that the external diameter of the outer sleeve 12 is fixed on a jaw ridge 19 and the external diameter of the inner sleeve 13 is fixed to a bone segment 21 which is moved away with respect to the outer sleeve 12. This could be provided, for example, in the reconstruction of a chin.

A preferred case of application of the distraction device 11 according to the invention is provided in FIG. 2. A lower jaw has a cataplasia 62 of the mandibular process, due to which an adequate dental prosthesis can no longer be produced. This is the case when, due to the cataplasia, the height of the jawbone is no longer sufficient for a stable anchoring of the prosthesis or to receive a denture foundation. The distraction device 11 according to the invention is used for the reconstruction of the jaw ridge 19 by vertical callus distraction. A bone cut is sawn into the jaw ridge 19, and is constituted in a trapezoidal shape as seen in plan, with the cut surfaces tapering toward the buccal cavity. Guiding of the bone segment 21 in the jaw ridge 19 can thereby be given. A bore is then set through the bone segment 21 and into the jaw ridge 19. After the cut, the bone segment 21 can advantageously be fixed to the jaw ridge 19 by auxiliary means before the bore for the distraction device 11 is made. Alternatively, it can also be provided that the bore is first put in place, and the bone cut is then performed.

If the distraction device 11 has a self-tapping thread, this is screwed directly into the bore. Otherwise, the bore can be tapped in a subsequent step. The distraction device is screwed in to an extent such that the abutment surface 26 is in contact with, or abuts on, the soft tissues and/ or bone.

Cases can arise in which an abutment of the mounting section 23 on the soft tissues and/or bone is not possible. In order to bring the outer sleeve 12 into contact with the soft tissues and/or bone in such cases, it is provided to arrange one or more distance washers in order to bridge over the space. The distance washers or distance pieces can have different thicknesses. A material such as that for the device can likewise be provided here. If one or more thread turns of the outer sleeve 12 are situated outside the soft tissues and/or the bone, a guard nut or the like can also be provided. The free space which may possibly result between the guard nut and the mounting section 23 can be closed by a corresponding sleeve or an intermediate piece, or can remain free.

The free end of the mounting section 23 faces toward the upper jaw, and is easily accessible, for example, by a tool wrench. After the distraction device 11 has been set in place, the callus distraction can begin after a short healing period of, for example, a week. A suitable rate of distraction is between 0.25 and 0.5 mm per day, so that a sufficient height of the jaw is attained after 14 days, for example. The healing tissue can thereafter mature. Provided that this has taken place, the further provision of a prosthesis can proceed. For example, the distraction device can be removed and an artificial tooth root can be inserted. Likewise, the distraction device can be constituted as a tooth root and can directly serve for the anchoring of a dental prosthesis.

The distraction device 11 according to the invention thus makes possible a callus distraction in which the mechanical application of forces takes place directly at the location, so that suitable force conditions are in effect. Furthermore, the problem of removal morbidity and its associated risks and discomfort are prevented. Moreover, the steps of the dental operation can be considerably minimized, particularly if the distraction device 11 serves as the dental prosthesis.

What is claimed is:

1. Device for the distraction of bone segments, particularly in the jaw region, with a first component (12) which is constituted as an outer sleeve and a second component (13) which is constituted as an at least partially inner sleeve which is at least partially arranged in the outer sleeve (12), with an adjusting device (14) by means of which the at least two components (12, 13), relatively displaceable with respect to each other, are adjustable for the increase of a distance relative to each other, the outer and inner sleeves (12, 13) being settable at least partially within the bone in a bore of a bone segment (19, 21), and the inner sleeve (13) engaging one bone segment (19) and the outer sleeve (12) engaging a further bone segment (21), wherein a respective section with an external thread (17, 16) is provided on the outer and inner sleeves (12, 13), and the outer sleeve (12) has a mounting section (23).

2. Device according to claim 1, wherein the maximum diameters of the outer and inner sleeves (12, 13) is equal to, or slightly smaller than, a diameter of a dental implant.

3. Device according to claim 1, wherein the external threads of the outer and inner sleeves (12, 13) are constituted equal in diameter.

4. Device according to claim 1, wherein a section of the external thread (17) of the outer sleeve (12) and a section of the external thread (16) of the inner sleeve (13) are mutually separated such that a constant thread pitch is provided.

5. Device according to claim 1, wherein the diameter of the external thread (17) of the outer sleeve (12) is constituted greater than the diameter of the inner sleeve (13).

6. Device according to claim 1, wherein the external thread (16, 17) is constituted as a self-tapping thread.

7. Device according to claim 1, wherein a guide section (32) of the inner sleeve (13) extending into the outer sleeve (12) is secured against torsion.

8. Device according to claim 1, wherein the mounting section (23) is constituted as a polygonal head.

9. Device according to claim 1, wherein a section (27) free from threads is provided between the external thread (17) of the outer sleeve (12) and the mounting section (23) is constituted greater in diameter than the section free from threads.

10. Device according to claim 9, wherein the section (27) free from threads is bounded by an annular shoulder (24) with a thereto directly adjoining stop shoulder (26), the annular shoulder (24) being constituted greater in diameter than the mounting section (23).

11. Device according to claim 9, wherein the section (27) free from threads and the stop surface (26) are polished.

12. Device according to claim 1, wherein the mounting section (23) is constituted as the receiving section for a liquid-tight closure cap or for a dental implant, the receiving section being constituted as an internal or external thread.

13. Device according to claim 1, wherein the outer and inner sleeves (12, 13) are constituted of biocompatible material, which has a minimum toughness for constituting the external threads (16, 17).

14. Device according to claim 13, wherein at least the inner and outer sleeve (12, 13) are constituted of titanium alloy.

15. Device according to claim 1, wherein the outer sleeve (12) and inner sleeve (13) are constituted such that the distraction device (11) set in a bore is constituted as medium-tight with respect to the bone segments (19, 21).

16. Device according to claim 1, wherein a mechanical adjusting device (14) is provided which includes a threaded spindle (41) which is rotationally connected via a thread (42) to an internal thread (43) of the inner sleeve (12), and a spindle head (44) of the threaded spindle (41) is fastened, axially immovable, to the outer sleeve.

17. Device according to claim 16, wherein the spindle head (44) is arranged axially at the free end of the mounting section (23) of the outer sleeve (12).

18. Device according to claim 16, wherein the outer sleeve (12) has a first bore section (31) which merges, in the region of the annular shoulder (24) and the mounting section (23), into a second bore section (34) of larger diameter and forms a first shoulder (46), and has a third bore section (36), enlarged with respect to the second bore section (34), and form a shoulder (47), the distance of the shoulder (46) to the shoulder (47) corresponding to at least the thickness of the spindle head (44).

19. Device according to claim 18, wherein a securing bushing is inserted into the third bore (36) and fixes the spindle head (44) of the threaded spindle (41) axially of the first shoulder.

20. Device according to claim 16, wherein a radial shaft seal (49), is provided between the outer sleeve (12) and the threaded spindle (41).

21. Device according to claim 16, wherein the inner sleeve (13) has, at its free end situated opposite to the outer sleeve (12), a closure cap (33) arranged to be medium-tight.

22. Device according to claim 21, wherein the closure cap (33) is pressed in, screwed in, or fixed by laser welding.

23. Device according to claim 16, wherein the threaded spindle (41) has, at its free end arranged in the inner sleeve (13), a locking element (52) which is constituted larger in diameter than a core diameter of the thread (42) of the threaded spindle (41).

24. Device according to claim 23, wherein the locking element (52) is pressed on or screwed on.

25. Device according to claim 16, wherein a material matching is provided between the inner sleeve (13) and the threaded spindle (41), the threaded spindle (41) being constituted of implant steel.

26. Device according to claim 1, wherein the adjusting device (14) is constituted as a compression spring mechanism, the maximum distraction path being determinable by its initial stress.

27. Device according to claim 1, wherein the adjusting device (14) is constituted as an osmotic pressure chamber with a semipermeable membrane.

28. Device according to claim 27, wherein the distraction path and the rate of distraction are adjustable by the concentration difference of a pressure medium.

29. Device according to claim 1, wherein the adjusting device (14) is adjustable with compressible materials, air, or a rubber-elastic material.

* * * * *

UNITED STATES PATENT AND TRADEMARK OFFICE
CERTIFICATE OF CORRECTION

PATENT NO. : 6,491,696 B1
DATED : December 10, 2002
INVENTOR(S) : Martin Kunkel

It is certified that error appears in the above-identified patent and that said Letters Patent is hereby corrected as shown below:

<u>Title page,</u>
Item [73], Assignee, make the following change from "Medicon Chirurgiemechaniker-Genossenschaft" to -- Medicon eG Chirurgiemechaniker-Genossenschaft --

Signed and Sealed this

Thirtieth Day of March, 2004

JON W. DUDAS
*Acting Director of the United States Patent and Trademark Office*